United States Patent
Gutin et al.

(10) Patent No.: US 11,225,685 B2
(45) Date of Patent: *Jan. 18, 2022

(54) METHODS AND MATERIALS FOR ASSESSING ALLELIC IMBALANCE

(71) Applicant: MYRIAD GENETICS, INC., Salt Lake City, UT (US)

(72) Inventors: Alexander Gutin, Salt Lake City, UT (US); Kirsten Timms, Salt Lake City, UT (US); Jerry Lanchbury, Salt Lake City, UT (US)

(73) Assignee: MYRIAD GENETICS, INC., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/815,963

(22) Filed: Mar. 11, 2020

(65) Prior Publication Data

US 2020/0239943 A1   Jul. 30, 2020

Related U.S. Application Data

(63) Continuation of application No. 15/412,404, filed on Jan. 23, 2017, now Pat. No. 10,626,449, which is a continuation of application No. 15/010,721, filed on Jan. 29, 2016, now Pat. No. 9,574,229, which is a continuation of application No. 14/109,163, filed on Dec. 17, 2013, now Pat. No. 9,279,156, which is a continuation of application No. PCT/US2012/042668, filed on Jun. 15, 2012.

(60) Provisional application No. 61/498,418, filed on Jun. 17, 2011.

(51) Int. Cl.
*C12Q 1/6827* (2018.01)
*G16B 30/00* (2019.01)
*C12Q 1/6858* (2018.01)
*C12Q 1/6874* (2018.01)
*C12Q 1/6883* (2018.01)

(52) U.S. Cl.
CPC ......... *C12Q 1/6827* (2013.01); *C12Q 1/6858* (2013.01); *C12Q 1/6874* (2013.01); *C12Q 1/6883* (2013.01); *G16B 30/00* (2019.02)

(58) Field of Classification Search
None
See application file for complete search history.

(56) References Cited

U.S. PATENT DOCUMENTS

| | | |
|---|---|---|
| 3,590,028 A | 6/1971 | Arcamone |
| 3,892,790 A | 7/1975 | Tobe |
| 3,904,663 A | 9/1975 | Tobe |
| 4,138,480 A | 2/1979 | Gosalvez |
| 4,946,954 A | 8/1990 | Talebian |
| 4,950,738 A | 8/1990 | King |
| 4,996,337 A | 2/1991 | Bitha |
| 5,091,521 A | 2/1992 | Kolar |
| 5,177,075 A | 1/1993 | Suto |
| 5,295,944 A | 3/1994 | Teicher |
| 5,434,256 A | 7/1995 | Khokhar |
| 5,445,934 A | 8/1995 | Fodor |
| 5,510,270 A | 4/1996 | Fodor |
| 5,527,905 A | 6/1996 | Sugimura |
| 5,539,083 A | 7/1996 | Cook |
| 5,556,752 A | 9/1996 | Lockhart |
| 5,578,832 A | 11/1996 | Trulson |
| 5,633,016 A | 5/1997 | Johnson |
| 5,633,243 A | 5/1997 | Sugimura |
| 5,744,305 A | 4/1998 | Fodor |
| RE36,397 E | 11/1999 | Zhang |
| 6,040,138 A | 3/2000 | Lockhart |
| 6,087,340 A | 7/2000 | Gatti |
| 6,210,891 B1 | 4/2001 | Nyren |
| 6,214,821 B1 | 4/2001 | Daoud |
| 6,258,568 B1 | 7/2001 | Nyren |
| 6,274,320 B1 | 8/2001 | Rothberg |
| 6,403,563 B1 | 6/2002 | Geroni |
| 6,455,258 B2 | 9/2002 | Bastian |
| 6,465,177 B1 | 10/2002 | Hoon |
| 6,534,293 B1 | 3/2003 | Barany |
| 7,351,701 B2 | 4/2008 | Helleday |
| 7,485,707 B2 | 2/2009 | Matvienko |
| 7,732,491 B2 | 6/2010 | Sherman |
| 7,754,684 B2 | 7/2010 | Stewart |
| 7,759,488 B2 | 7/2010 | Xiao |
| 7,759,510 B2 | 7/2010 | Kay |
| 7,858,331 B2 | 12/2010 | D Andrea |
| 7,860,840 B2 | 12/2010 | Johnson |
| 7,868,040 B2 | 1/2011 | Wilson |

(Continued)

FOREIGN PATENT DOCUMENTS

| | | |
|---|---|---|
| EP | 0430402 | 6/1991 |
| EP | 1260520 | 11/2002 |

(Continued)

OTHER PUBLICATIONS

"Myriad's HRD Test Significantly Predicts Response to Cisplatin Treatment in Patients With Triple Negative Breast Cancer in Second Research Study", (Dec. 14, 2013), Myriad, URL: http://files.shareholder.com/downloads/MYGN/3039924177x0x713818/74F0EC3E-B337-4724-A51B-63BA3BD75A08/MYGN_News_2013_12_14_General.pdf, (Oct. 19, 2016), XP055312045.

Abkevich et al., "Patterns of genomic loss of heterozygosity predict homologous recombination repair defects in epithelial ovarian cancer", British Journal of Cancer, vol. 107, No. 10, Oct. 9, 2012, pp. 1776-1782.

(Continued)

*Primary Examiner* — Ethan C Whisenant
(74) *Attorney, Agent, or Firm* — FisherBroyles, LLP; Victoria L. Boyd; Jason M. Pass

(57) ABSTRACT

Methods and systems for detecting allelic imbalance using nucleic acid sequencing are provided.

20 Claims, 3 Drawing Sheets

(56) References Cited

U.S. PATENT DOCUMENTS

| | | | |
|---|---|---|---|
| 7,915,280 B2 | | 3/2011 | Ferraris |
| 9,279,156 B2* | | 3/2016 | Gutin .................. C12Q 1/6827 |
| 9,512,485 B2 | | 12/2016 | Richardson |
| 9,574,229 B2* | | 2/2017 | Gutin .................. C12Q 1/6827 |
| 10,190,160 B2 | | 1/2019 | Szallasi |
| 10,612,098 B2* | | 4/2020 | Abkevich .............. A61P 43/00 |
| 10,626,449 B2* | | 4/2020 | Gutin .................. C12Q 1/6858 |
| 2003/0049613 A1 | | 3/2003 | Perucho |
| 2005/0112604 A1 | | 5/2005 | Fujimoto |
| 2006/0088870 A1 | | 4/2006 | Finkelstein |
| 2007/0004621 A1* | | 1/2007 | Shridhar .............. C12Q 1/6886 |
| | | | 514/44 R |
| 2007/0070349 A1 | | 3/2007 | Harris |
| 2008/0108057 A1* | | 5/2008 | Griffith ............... C12Q 1/6886 |
| | | | 435/6.14 |
| 2008/0262062 A1 | | 10/2008 | Ossovskaya |
| 2009/0081237 A1 | | 3/2009 | D Andrea |
| 2009/0246789 A1* | | 10/2009 | Buckhaults ......... C12Q 1/6886 |
| | | | 435/6.14 |
| 2010/0130527 A1 | | 5/2010 | Lehrer |
| 2010/0145894 A1 | | 6/2010 | Semizarov |
| 2010/0159466 A1 | | 6/2010 | Eng |
| 2012/0015050 A1 | | 1/2012 | Abkevich |
| 2013/0281312 A1 | | 10/2013 | Richardson |
| 2014/0363521 A1 | | 12/2014 | Abkevich |
| 2015/0080260 A1 | | 3/2015 | Abkevich |

FOREIGN PATENT DOCUMENTS

| | | |
|---|---|---|
| EP | 2981624 A2 | 2/2016 |
| KR | 20040102024 | 12/2004 |
| KR | 100925337 B1 | 11/2009 |
| KR | 20100058566 | 6/2010 |
| WO | 9520952 | 8/1995 |
| WO | 9841531 | 9/1998 |
| WO | 9954498 | 10/1999 |
| WO | 0024933 | 5/2000 |
| WO | 03074723 A2 | 9/2003 |
| WO | 2004042032 | 5/2004 |
| WO | 2004075833 | 9/2004 |
| WO | 2006098978 | 9/2006 |
| WO | 2006110855 | 10/2006 |
| WO | 2006116341 | 11/2006 |
| WO | 2006128195 | 11/2006 |
| WO | 2007035893 | 3/2007 |
| WO | 2009033178 | 3/2009 |
| WO | 2009073869 | 6/2009 |
| WO | 2009148528 | 12/2009 |
| WO | 2010028288 | 3/2010 |
| WO | 2010051318 | 5/2010 |
| WO | 2011048495 | 4/2011 |
| WO | 2011106541 | 9/2011 |
| WO | WO-2011-160063 A2 * | 12/2011 |
| WO | 2012019000 | 2/2012 |
| WO | 2012027224 | 3/2012 |
| WO | 2012092426 A1 | 7/2012 |
| WO | 2013096843 A1 | 6/2013 |
| WO | 2013130347 A1 | 9/2013 |
| WO | 2013182645 | 12/2013 |
| WO | 2014165785 | 10/2014 |
| WO | 2015086473 A1 | 6/2015 |
| WO | 2015108986 A1 | 7/2015 |

OTHER PUBLICATIONS

Abkevich et al., "Supplemental Material: Table S1: Validation of copy number determinations by Real Time PCR SNP ID Adjacent Gene Sample Copy Number by Real-Time PCR Copy Number by CCNT SNP A",-1712744 CDKN2A HF505 0.010 0.47 HF1382 0.14 0, Oct. 1, 2006, pp. 5-1713144, XP055085899, Retrieved from the Internet: URL: http://cancerres.aacrjournals.org/content/suppl/2006/10/04/66.19.9428.DC2/Supplementary-Tables-1-5.pdf [retrieved on Oct. 29, 2013].

Al-Mulla et al., "Metastatic recurrence of early-stage colorectal cancer is linked to loss of heterozygosity on Chromosomes 4 and 14q" Journal of Clinical Pathology, vol. 59, No. 6, pp. 624-630 (2006).

Argos et al., "Genomewide scan for loss of heterozygosity and chromosomal amplification in breast carcinoma using single-nucleotide polymorphism arrays", Cancer Genetics and Cytogenetics, vol. 182, No. 2, Apr. 15, 2008, pp. 69-74.

Artt et al., "BRCA1 is Required for Common-Fragile-Site Stability via Its G2/M Checkpoint Function," Molecular and Cellular Biology, Aug. 2004, 24(15): 6701-6709.

Ashworth, "A Synthetic Lethal Therapeutic Approach: Poly(ADP) Ribose Polymerase Inhibitors for the Treatment of Cancers Deficient in DNA Double-Strand Break Repair," Journal of Clinical Oncology, Aug. 2008, 26(22): 3785-3790.

Audeh et al., "Novel Treatment Strategies in Triple-Negative Breast Cancer: Specific Role of Poly(adenosine Diphosphate-Ribose) Polymerase Inhibition", Pharmacogenomics and Personalized Medicine, vol. 7, 2014, pp. 307-316.

Bamford et al., "The COSMIC (Catalogue of Somatic Mutations in Cancer) database and website," British Journal of Cancer, 2004, 91: 355-358.

Beder et al., "Genome-wide analyses on loss of heterozygosity in head and neck squamous cell carcinomas", Laboratory Investigation, vol. 83, No. 1, 2003, pp. 99-105, XP002703165.

Bell et al., "Integrated genomic analyses of ovarian carcinoma," Nature, Jun. 2011, 474: 609-615.

Bengtsson et al., "A single-array preprocessing method for estimating full-resolution raw copy numbers from all Affymetrix genotyping arrays including GenomeWideSNP 5 & 6", Bioinformatics, 2009, 25: 2149-2156.

Bengtsson et al., "TumorBoost: Normalization of allele-specific tumor copy numbers from a single pair of tumor-normal genotyping microarrays", BMC Bioinformatics 11:245-262 (2010).

Bernardini et al., "The use of cytogenetics in understanding ovarian cancer", Biomedicine and Pharmacotherapy, 2004, 58: 17-23.

Beroukhim et al., "Assessing the significance of chromosomal aberrations in cancer: methodology and application to glioma", Proc. Natl. Acad. Sci. U.S.A., 104(50):20007-12, Dec. 2007.

Beroukhim et al., "Inferring Loss-of-Heterozygosity from Unpaired Tumors Using High-Density Oligonucleotide SNP Arrays", Bioinformatics, vol. 19, No. 5, Jan. 1, 2006 (Jan. 1, 2006), p. 2397.

Birkbak et al., "Abstract 4823: Copy number gain and increased expression of BLM and FANCI is associated with sensitivity to genotoxic chemotherapy in triple negative breast and serous ovarian cancer", Cancer Res., 72(8): 1, Apr. 15, 2012, 1 page.

Birkbak et al., "Paradoxical relationship between chromosomal instability and survival outcome in cancer", Cancer Res, May 2011, 71(10): 3447-3452.

Birkbak et al., "Telomeric allelic imbalance indicates defective DNA repair and sensitivity to DNA-damaging agents", Cancer Discov; 2012; 2(4): 366-375; doi: 10.1158/2159-8290.CD-11-0206.

Bouwman et al., "53BP1 loss rescues BRCA1 deficiency and is associated with triple-negative and BRCA-mutated breast cancers", Nature Structural & Molecular Biology, Jun. 2010, 17(6): 688-696.

Bryant et al., "Specific killing of BRCA2-deficient tumours with inhibitors of poly(ADP-ribose) polymerase", Nature; 2005; 434(7035):913-917.

Buch H N et al., "Prediction of recurrence of nonfunctioning pituitary tumours by loss of heterozygosity analysis", Clinical Endocrinology, vol. 61, 2004, p. 19-22, XP002703163.

Bunting et al., "53BP1 inhibits homologous recombination in Brca1-deficient cells by blocking resection of DNA breaks", Cell, Apr. 2010, 141(2): 243-254.

Burger et al., "Drug transporters of platinum-based anticancer agents and their clinical significance", Drug Resistance Updates, 2011, 14: 22-34.

Byrski et al., "Response to neoadjuvant therapy with cisplatin in BRCA1-positive breast cancer patients", Breast Cancer Res Treat, 2009, 115: 359-363.

Calvert et al., "245 Invited PARP inhibitors in cancer treatment", European Journal of Cancer. Supplement, Pergamon, Oxford, GB, vol. 6, No. 12, Oct. 1, 2008, p. 80.

(56) References Cited

OTHER PUBLICATIONS

Campbell et al., "A genetic variant that disrupts MET transcription is associated with autism", PNAS, Nov. 2006, 103: 16834-16839.
Carr et al., "High-resolution analysis of allelic imbalance in neuroblastoma cell lines by single nucleotide polymorphism arrays", Cancer Genetics and Cytogenetics, 2007, 172: 127-138.
Cass et al., "Improved Survival in Women with BRCA-Associated Ovarian Carcinoma", Cancer, May 2003, 97(9): 2187-2195.
Cerbinskaite et al., "Defective homologous recombination in human cancers", Cancer Treat Rev; 2012; Epub 2011; 38(2): 89-100.
Cha et al., "ATR Homolog Mec1 Promotes Fork Progression, Thus Averting Breaks in Replication Slow Zones", Science, Jul. 2002, 297: 602-606.
Chang et al., "Assessment of Plasma DNA Levels, Allelic Imbalance, and CA125 as Diagnostic Tests for Cancer", Journal of the National Cancer Institute, Nov. 2002, 94(22): 1697-1703.
Cheung et al., "Clinicopathologic significance of loss of heterozygosity on chromosome 1 in cervical cancer", Gynecologic Oncology, Academic Press, London, GB, vol. 96, No. 2, Feb. 1, 2005, pp. 510-515, XP027205508, ISSN: 0090-8258 [retrieved on Jan. 18, 2005].
Choi et al., "Genetic Classification of Colorectal Cancer Based on Chromosomal Loss and Microsatellite Instability Predicts Survival", Clinical Cancer Research, Jul. 2002, 8:2311-2322.
Dann et al., "BRCA1/2 mutations and expression: response to platinum chemotherapy in patients with advanced stage epithelial ovarian cancer", Gynecol Oncol; 2012;125(3):677-682.
De Preter et al., "Application of laser capture microdissection in genetic analysis of neuroblastoma and neuroblastoma precursor cells", Cancer Letters, 2003, 197: 53-61.
De Soto et al., "The Inhibition and Treatment of Breast Cancer with Poly (ADP-ribose) Polymerase (PARP-1) Inhibitors", Int. J. Biol. Sci., 2006, 179-185.
Duncavage et al., "Hybrid Capture and Next-Generation Sequencing Identify Viral Integration Sites From Formalin-Fixed, Paraffin-Embedded Tissue", The Journal of Molecular Diagnostics, 2011, vol. 13, No. 3, pp. 325-333.
Edwards et al., "Resistance to therapy caused by intragenic deletion in BRCA2", Nature; 2008; 451(7182):1111-1115.
Etemadmoghadam et al., "Integrated Genome-Wide DNA Copy Number and Expression Analysis Identifies Distinct Mechanisms of Primary Chemoresistance in Ovarian Carcinomas", Clin Cancer Res, 2009, 15: 1417-1427.
Fang et al., "Genomic Differences Between Estrogen Receptor (ER)-Positive and ER-Negative Human Breast Carcinoma Identified by Single Nucleotide Polymorphism Array Comparative Genome Hybridization Analysis", Cancer, (May 2011), vol. 117, No. 10, pp. 2024-2034, XP002741861.
Farmer et al., "Targeting DNA repair defect in BRCA mutant cells as a therapeutic strategy", Nature; 2005; 434 (7035):917-921.
Feltmate et al., "Whole-genome allelotyping identified distinct loss-of-heterozygosity patterns in mucinous ovarian and appendiceal carcinomas", Clinical Cancer Research, vol. 11, No. 21, Nov. 1, 2005, pp. 7651-7657XP002703164.
Ferreira et al., "Array CGH and gene-expression profiling reveals distinct genomic instability patterns associated with DNA repair and cell-cycle checkpoint pathways in Ewing's sarcoma", Oncogene, vol. 27, No. 14, Mar. 27, 2008, pp. 2084-2090, XP55010742, ISSN: 0950-9232DOI: 10.1038/sj.onc.1210845.
Filopanti et al., "Loss of heterozygosity at the SS receptor type 5 locus in human GH- and TSH-secreting pituitary adenomas", J. Endocrinol. Invest., (Nov. 2004), vol. 27, No. 10, pp. 937-942, XP008120366.
Fontanillas et al., "Key considerations for measuring allelic expression on a genomic scale using high-throughput sequencing", Molecular Ecology, vol. 19, No. 1, Mar. 1, 2010, pp. 212-227.
Franko et al., "Loss of heterozygosity predicts poor survival after resection of pancreatic adenocarcinoma", J. Gastrointest. Surg., Oct. 2008, vol. 12, No. 10, pp. 1664-1723.
Friedenson, Bernard, "BRCA1 and BRCA2 pathways and the risk of cancers other than breast or ovarian", MedGenMed; 2005; 7(2):60, 25 pages.
Gelmon et al., "Olaparib in patients with recurrent high-grade serous or poorly differentiated ovarian carcinoma or triple-negative breast cancer: a phase 2, multicentre, open-label, non-randomised study", Lancet Oncol; 2011;12(9):852-861.
Gnirke et al., "Solution hybrid selection with ultra-long oligonucleotides for massively parallel targeted sequencing", Nat Biotechnol. Feb. 2009;27(2):182-9. doi: 10.1038/nbt.1523. Epub Feb. 1, 2009.
Goransson et al., "Quantification of normal cell fraction and copy number neutral LOH in clinical lung cancer samples using SNP array data", PLoS One; 2009; 4(6):e6057; doi: 10.1371/ journal. pone.0006057, 10 pages.
Gorringe et al., "Are There Any More Ovarian Tumor Suppressor Genes? A New Perspective Using Ultra High-Resolution Copy Number and Loss of Heterozygosity Analysis", Genes, Chromosones & Cancer, 2009, 48: 931-942.
Graziani et al., "PARP-1 inhibition to treat cancer, ischemia, inflammation", Pharmacological Research, Academic Press, London, GB, vol. 52, No. 1, Jul. 1, 2005, pp. 1-4, XP004902631, ISSN: 1043-6618DOI: 10.1016/J.PHRS.2005.02.007.
Gudmundsdottir et al., "The roles of BRCA1 and BRCA2 and associated proteins in the maintenance of genomic stability", Oncogene, 2006, 25: 5864-5874.
Gunnarsson et al., "Large but not small copy-number alterations correlate to high-risk genomic aberrations and survival in chornic lymphocytic leukemia: a high-resolution genomic screening of newly diagnosed patients", Leukemia, 2010, 24: 211-215.
Halper-Stromberg et al., "Performance assessment of copy number microarray platforms using a spike-in experiment", Bioinformatics. Apr. 15, 2011;27(8):1052-60. doi: 10.1093/bioinformatics/btr106.
Haluska et al., "HomologJus recombination deficiency (HRD) score and niraparib efficacy in high grade ovarian cancer", European Journal of Cancer, 2014, vol. 50 Supplement, pp. 72-73.
Hampton et al., "Simultaneous assessment of loss of heterozygosity at multiple microsatellite loci using semi-automated fluorescence-based detection: subregional mapping of chromosome 4 in cervical carcinoma", Proc. Natl. Acad. Sci. U. S. A., (Jun. 25, 1995), vol. 93, No. 13, pp. 6704-6709, XP055085426.
Hansen et al., "Clinical significance of homologous recombination deficiency score testing in endometrial cancer patients", 2016, ASCO presentation.
Hastings et al., "A Microhomology-Mediated Break-Induced Replication Model for the Origin of Human Copy Number Variation", PLoS Genetics, Jan. 2009, 5(1): 1-9, el000327.
Hastings et al., "Mechanisms of change in gene copy number", Nat Rev Genet, Aug. 2009, 10(8): 551-564.
Heap et al., "Genome-wide analysis of allelic expression imbalance in human primary cells by high-throughput transcriptome resequencing", Human Molecular Genetics, vol. 19, No. 1, Jan. 1, 2010, pp. 122-134.
Hedges et al., "Comparison of three targeted enrichment strategies on the SOLiD sequencing platform", PLoS One. Apr. 29, 2011;6(4):e18595. doi: 10.1371/journal.pone.0018595.
Heinsohn et al., "Determination of the prognostic value of loss of heterzygosity at the retinoblastoma gene in osteosarcoma", Int. J. Oncol., May 2007, vol. 30, No. 5, pp. 1205-1214.
Heiser et al., "Subtype and pathway specific responses to anticancer compounds in breast cancer", PNAS, Feb. 2012, 109(8): 2724-2729.
Hendricks et al., "'Recombmice': The past, present, and future of recombination-detection in mice", DNA Repair, vol. 3 No. 10, Oct. 5, 2004, pp. 1255-1261.
Hennessy et al., "Somatic mutations in BRCA1 and BRCA2 could expand the number of patients that benefit from poly (ADP ribose) polymerase inhibitors in ovarian cancer", Journal of Clinical Oncology, (Jul. 6, 2010), vol. 28, No. 22, pp. 3570-3576, XP055070076.
Hodgson et al., "Candidate Biomarkers of PARP Inhibitor Sensitivity in Ovarian Cancer Beyond the BRCA Genes", Br J Cancer. Nov. 2018;119(11):1401-1409.

(56) References Cited

OTHER PUBLICATIONS

Holstege et al., "BRCA1-mutated and basal-like breast cancers have similar aCGH profiles and a high incidence of protein truncating TP53 mutations", BMC Cancer; 2010; 10:654, 15 pages.
Horiuchi et al., "Epigenetic Changes during Ovarian Cancer Development and Progression—BRCAI Mehylation and SI00A4 Hypomethylation", Acta Obstetrica et Gynaecologica Japonica, 2008, vol. 60, No. 11, pp. 1844-1854.
Iafrate et al., "Detection of large-scale variation in the human genome", Nature Genetics, Sep. 2004, 36(9): 949-951.
International Search Report and Written Opinion from Application No. PCT/US2014/033014, dated Aug. 12, 2014, 6 pages.
International Search Report and Written Opinion from Application No. PCT/US2015/064473, dated Apr. 14, 2016, 14 pages.
International Search Report and Written Opinion in Internation Application No. PCT/US2011/040953, dated Feb. 27, 2012, 11 pages.
International Search Report in International Application No. PCT/US2017/023152, dated Jun. 7, 2017, 16 pages.
International Search Report, for application PCT/EP2013/061707, dated Jul. 29, 2013.
International Search Report, for application PCT/EP2014/076786, dated Feb. 27, 2015.
International Search Report, for application PCT/US2011/026098, dated Nov. 25, 2011.
International Search Report, for application PCT/US2011/040953 dated Feb. 27, 2012.
International Search Report, for application PCT/US2011/048427 dated Nov. 7, 2011.
International Search Report, for application PCT/US2012/042668, dated Feb. 1, 2013.
International Search Report, for application PCT/US2012/071380 dated Apr. 12, 2013.
International Search Report, for application PCT/US2013/027295 dated Jun. 10, 2013.
Isakoff et al., "TBCRC009: A Multicenter Phase II Clinical Trial of Platinum Monotherapy With Biomarker Assessment in Metastatic Triple-Negative Breast Cancer", J Clin Oncol, 2015, 1-8.
Jacobs et al., "Genome-wide, High-Resolution Detection of Copy Number, Loss of Heterozygosity, and Genotypes From Formalin-Fixed, Paraffin-Embedded Tumor Tissue Using Microarrays", Cancer Research, 2007, vol. 67, No. 6, pp. 2544-2551.
Janne et al., "High-resolution single-nucleotide polymorphism array and clustering analysis of loss of heterozygosity in human lung cancer cell lines", Oncogene, vol. 23, No. 15, Mar. 29, 2004 (Mar. 29, 2004), pp. 2716-2726.
Jelovac, D. and Armstrong, D.K., "Recent Progress in the Diagnosis and Treatment of Ovarian Cancer", CA Cancer J Clin, 61/3, pp. 183-203, https://doi.org/10.3322/caac.20113, Apr. 26, 2011 (Apr. 26, 2011).
Ji and Welch, "Molecular inversion probe assay for allelic quantitation", Methods Mol Biol. 2009;556:67-87. doi: 10.1007/978-1-60327-192-9_6.
Johansson et al., "Abstract 4833: A genomic portrait of tumor progression using next-generation sequencing", Cancer Res., Apr. 15, 2011, vol. 71, p. 4833.
Johansson et al., "Targeted resequencing of candidate genes using selector probes," Nucleic Acids Research, 2011, 39: 1-13.
Joosse et al., "Prediction of BRCA1-association in hereditary non-BRCAI/2 breast carcinomas with array-CGH", Breast Cancer Res Treat, 2009, 116:479-489.
Juul et al., "A Genomic Profile Derived Summary Measure of Chromosomal Breakpoints Predicts Response to Treatment with the DNA-Damaging Agent Cisplatin", Cancer Research, 69(24): 509S-510S (2009).
Juul et al., "Amount of Allelic Imbalance Predicts Response to Cisplatin in Breast and Ovarian Cancer", Annals of Oncology 21 (2010).
Juul et al., "Amount of Allelic Imbalance Predicts Response to Cisplatin in Breast and Ovarian Cancer", Annals of Oncology, May 2010, 21: 1 page abstract.
Kaklamani et al., "Phase II neoadjuvant clinical trial of carboplatin and eribulin in women with triple negative early-stage breast cancer (NCT01372579)", Breast Cancer Res Treat, 2015, 151:629-638.
Kalb et al., "Fanconi Anemia: Causes and Consequences of Genetic Instability", Genome Dyn. Basel, Karger, 2006, 1: 218-242.
Kamat et al., "Chemotherapy induced microsatellite instability and loss of heterozygosity in chromosomes 2, 5, 10, and 17 in solid tumor patients", Cancer Cell International, 2014, 14: 118.
Kerangueven et al., "Genome-wide Search for Loss of Heterozygosity Shows Extensive Genetic Diversity of Human Breast Carcinomas", Cancer Research, 57(24):5469-5475 (1997).
Kiialainen et al., "Performance of Microarray and Liquid Based Capture Methods for Target Enrichment for Massively Parallel Sequencing and SNP Discovery", PLoS ONE, Feb. 2011, 6:e16486.
Kissel et al., "Translation of an STR-based biomarker into a clinically compatible SNP-based platform for loss of heterozygosity", Cancer Biomark. 2009;5(3):143-58. doi: 10.3233/CBM-2009-0618.
Kissel et al., "Translation of an STR-based biomarker into a clinically compatible SNP-based platform for loss of heterozygosity", Cancer Biomark. 2009;5(3):143-58. doi: 10.3233/CBM-2009-0618. Supplemental Table S1.
Knights et al., "Abstract A114: Preclinical evaluation of the PARP inhibitor olaparib in homologous recombination deficient (HRD) MRE11 mutant microsatellite instable (MSI) colorectal cancer", Mol Cancer Ther 2009;8(12 Suppl):A114.
Ko et al., "Frequent loss of heterozygosity on multiple chromosomes in Chinese esophageal squamous cell carcinomas", Cancer Letters, vol. 170, No. 2, pp. 131-138 (2001).
Kolomietz et al., "The Role of Alu Repeat Clusters as Mediators of Recurrent Chromosomal Aberrations in Tumors", Genes, Chromosomes & Cancer, 2002, 35: 97-112.
Kudoh et al., "Gains of 1q21-q22 and 13ql2-ql4 are Potential Indicators for Resistance to Cisplatin-based Chemotherapy in Ovarian Cancer Patients", Clinical Cancer Research, Sep. 1999, 5:2526-2531.
Kujawski et al., "Genomic complexity identifies patients with aggressive chronic lymphocytic leukemia", Blood, Sep. 2008, 112(5): 1993-2003.
Laframboise, Thomas, "Single nucleotide polymorphism arrays: a decade of biological, computational and technological advances", Nucleic Acids Res. Jul. 2009;37(13):4181-93. doi: 10.1093/nar/gkp552. Epub Jul. 1, 2009.
Lakhani et al., "Prediction of BRCA1 Status in Patients with Breast Cancer Using Estrogen Receptor and Basal Phenotype", Clin Cancer Res, Jul. 2005, 11(14): 5175-5180.
Ledermann et al., "Olaparib Maintenance Therapy in Platinum-Sensitive Relapsed Ovarian Cancer", N Engl J Med, 2012, 366: 1382-92.
Lemta et al., "Loss of Heterozygosity at 6q is Frequent and Concurrent with 3p Loss in Sporadic and Familial Capillary Hemangioblastomas", J. Neuropathol. Exp. Neurol., Oct. 2004, vol. 63, No. 10, pp. 1072-1079.
Leunen et al., "Recurrent Copy Number Alterations in BRCA1-Mutated Ovarian Tumors Alter Biological Pathways", Human Mutation, 2009, 30(12): 1693-702.
Lheureux et al., "Long-term responders of olaparib maintenance in high-grade serous ovarian cancer: Clinical and molecular characterization", Clin Cancer Res. Aug. 1, 2017;23(15):4086-4094. doi: 10.1158/1078-0432.CCR-16-2615. Epub Feb. 21, 2017.
Li et al., "Amplification of LAPTM4B and YWHAZ contributes to chemotherapy resistance and recurrence of breast cancer", Nature Medicine, Feb. 2010, 16(2): 214-219.
Li et al., "Direct inference of SNP heterozygosity rates and resolution of LOH detection", PLoS Comput Biol. Nov. 2007;3(11):e244. doi: 10.1371/journal.pcbi.0030244.
Li et al., "Jetset: selecting the optimal microarray probe set to represent a gene", Bioinformatics, 2011, 12: 474.
Li et al., "Major copy proportion analysis of tumor samples using SNP arrays", BMC Bioinformatics, 2008, 9:204, pp. 1-16.

(56) References Cited

OTHER PUBLICATIONS

Lieberfarb et al., "Genome-wide loss of heterozygosity analysis from laser capture microdissected prostate cancer using single nucleotide polymorphic allele (SNP) arrays and a novel bioinformatics platform dChipSNP", Cancer Res. Aug. 15, 2003;63(16):4781-5.
Lin et al., "Integrated analysis of copy number alterations and loss of heterozygosity in human pancreatic cancer using a high-resolution, single nucleotide polymorphism array", Oncology, vol. 75, No. 1-2, Sep. 1, 2008, pp. 102-112.
Loveday et al., "Germline mutations in RAD51D confer susceptibility to ovarian cancer", Nat Genet; 2011; 43(9):879-882.
Luo et al., "Cancer predisposition caused by elevated mototic recombination in Bloom mice", Nature Genetics, Dec. 2000, 26: 424-429.
Maeck et al., "Genetics instability in myelodysplastic syndrome: Detection of microsatellite instability and loss of heterozygosity in bone marrow samples with karyotype alterations", British Journal of Haematology, vol. 109, No. 4, Jun. 2000, pp. 842-846.
Marsit et al., "Inactivation of the Fanconi anemia/BRCA pathway in lung and oral cancers: implications for treatment and survival", Oncogene; 2004; 23(4): 1000-1004.
Mateo et al., "Appraising iniparib, the PARP inhibitor that never was—what must we learn?", Nature, Dec. 2013, 10: 688-696.
Matsumoto et al., "Allelic imbalance at 1P36 may predict prognosis of chemoradiation therapy for bladder preservation in patients with invasive bladder cancer", British Journal of Cancer, vol. 91, No. 6, pp. 1025-1031 (2004).
McVean, "What drives recombination hotspots to repeat DNA in humans?", Phil. Trans. R. Soc. B, 2010, 365:1213-1218.
Meadows et al., "Genome-wide analysis of loss of heterozygosity and copy number amplification in uterine leiomyomas using the 100K single nucleotide polymorphism array", Experimental and Molecular Pathology, vol. 91, No. 1, Apr. 8, 2011, pp. 434-439, XP028239924, ISSN: 0014-4800, DOI: 10.1016/J.YEXMP.2011.03.007 [retrieved on Apr. 8, 2011].
Medri et al., "Prognostic Relevance of Mitotic Activity in Patients With Node-Negative Breast Cancer", Modern Pathology, 2003, 16(11):1067-1075.
Mei et al., "Genome-wide Detection of Allelic Imbalance Using Human SNPs and High-density DNA Arrays", Genome Research, 2000, 10: 1126-1137.
Meindl et al., "Germline mutations in breast and ovarian cancer pedigrees establish RAD51C as a human cancer susceptibility gene", Nature Genetics, May 2010, 42(5):410-416.
Mendes-Pereira et al., "Synthetic lethal targeting of PTEN mutant cells with PARP inhibitors", EMBO Mol Med; 2009; 1 (6-7): 315-322.
Mills et al., "Homologous Recombination Deficiency (HRD) Score Shows Superior Association with Outcome Compared to its Individual Score Components (LOH, TAI, and LST Scores) in Platinum Treated Serous Ovarian Cancer", Annual Meeting on Women's Cancer, 2016, pp. 1-19.
Mukhopadhyay et al., "Clinicopathological Features of Homologous Recombination-Deficient Epithelial Ovarian Dancers: Sensitivity to PARP Inhibitors, Platinum, and Survival", Cancer Research, 2012, 5675-5682.
Murayama-Hosokawa et al., "Genome-wide single-nucleotide polymorphism arrays in endometrial carcinomas associate extensive chromosomal instability with poor prognosis and unveil frequent chromosomal imbalances involved in the PI3-kinase pathway", Oncogene, Apr. 1, 2010, vol. 29, No. 13, pp. 1897-1908.
Nannya et al., "A robust algorithm for copy number detection using high-density oligonucleotide single nucleotide polymorphism genotyping arrays", Cancer Res; 2005; 65(14):6071-6079.
Narayan et al.; "Frequent promoter of methylation of CDH1, DAPK, RARB, and HIC1 genes in carcinoma of cervix uteri: its relationship to clinical outcome", Mol Cancer; 2003; 2:24, 12 pages.

Norquist et al., "Secondary somatic mutations restoring BRCA1/2 predict chemotherapy resistance in hereditary ovarian carcinomas", J Clin Oncol;2011; 29(22): 3008-3015.
Novak et al., "A high-resolution allelotype of B-cell chronic lymphocytic leukemia (B-CLL)", Blood, Sep. 2002, 100(5): 1787-1794.
O'Brien et al., "Converting cancer mutations into therapeutic opportunities", EMBO Mol. Med. 1:297-299 (2009).
O'Shaugnessy et al., "Iniparib plus chemotherapy in metastatic triple-negative breast cancer", N Engl J Med; 2011; 364(3):205-214.
Ogston et al., "A new histological grading system to neoadjuvant assess response of breast cancers to primary chemotherapy: prognostic significance and survial", The Breast, 2003, 12: 320-327.
Osborne et al., "A Genome-wide Map Showing Common Regions of Loss of Heterozygosity/Allelic Imbalance in Breast Cancer", Cancer Res, 2000, 60: 3706-3712.
Ott et al., "Chromosomal instability rather than p53 mutation is associated: with response to neoadjuvant cisplatin-based chemotherapy in gastric carcinoma", Clinical Cancer Research, The American Association for Cancer Research, US, 9(6):2307-2315 (2003).
Patel et al., "Failure of Iniparib to Inhibit Poly(ADP-Ribose) Polymerase in Vitro", Clin Cancer Res, Mar. 2012, 1655-1662.
Patoc et al., "Breast-cancer stromal cells with TP53 mutations and nodal metastases", N. Engl. J. Med., 2007, vol. 357, pp. 2543-2551.
Peng et al., "Genome-wide transcriptome profiling of homologous recombination DNA repair", Nature Communications 2014, 1-11.
Penning et al., "Discovery and SAR of 2-(1-propylpiperidin-4-yl)-1H-benzimidazole-4-carboxamide: A potent inhibitor of poly(ADP-ribose) polymerase (PARP) for the treatment of cancer", Bioorganic & Medicinal Chemistry, Pergamon, GB, vol. 16, No. 14, Jul. 15, 2008, pp. 6965-6975.
Pfeifer et al., "Genome-wide analysis of DNA copy number changes and LOH in CLL using high-density SNP arrays", Blood, vol. 109, No. 3, Oct. 5, 2006 (Oct. 5, 2006), pp. 1202-1210.
Popova et al., "Genome Alteration Print (GAP): a tool to visualize and mine complex cancer genomic profiles obtained by SNP arrays", Genome Biology, Biomed Central Ltd., London, GB, vol. 10, No. 11, Nov. 11, 2009, p. R128.
Popva et al., "Ploidy and Large-Scale Genomic Instability Consistently Identify Basal-like Breast Carcinomas with BRCAI/2 Inactivation", Cancer Research, Nov. 1, 2012, 72(21); 5454-62.
Puliti et al., "Low-copy repeats on chromosome 22q11.2 show replication timing switches, DNA flexibility peaks and stress inducible asynchrony, sharing instability features with fragile sites", Mutat Res. 686(1-2):74-83 (2010).
Rakha et al., "Basal-Like Breast Cancer: A Critical Review", Journal of Clinical Oncology, May 2008, 26(15): 2568-2581.
Ramirez et al., "Loss of 1p, 19q, and 10q heterozygosity prospectively predicts prognosis of oligodendroglial tumors-towards individualized tumor treatment?", Neuro. Oncol., May 2010, vol. 12, No. 5, pp. 490-499.
Rauch et al., "Molecular karyotyping using an SNP array for genomewide genotyping", Journal of Medical Genetics, 2004, 41:916-922.
Richard et al., "Comparative Genomics and Molecular Dynamics of DNA Repeats in Eukaryotes", Microbiology and Molecular Biology Reviews, Dec. 2008, 686-727.
Richardson et al., "X chromosomal abnormalities in basal-like human breast cancer", Cancer Cell, Feb. 2006, 9:121-132.
Roscillli et al., "Annual Meeting of the American Association for Cancer Research", Apr. 17-21, 2010, No. 685, 5 pages.
Ross and Cronin, "Whole cancer genome sequencing by next-generation methods", Am J Clin Pathol. Oct. 2011;136(4):527-39. doi: 10.1309/AJCPR1SVT1VHUGXW.
Ross et al., "Comprehensive next-generation sequencing for clinically actionable mutations from formalin-fixed cancer tissues", Journal of Clinical Oncology, 2011, 15 Supp: 1-3, abstract.
Ryan et al., "Neoadjuvant cisplatin and bevacizumab in triple negative breast cancer (TNBC): Safety and efficacy", 2009 ASCO Annual Meeting, http://meetinglibrary.asco.org/content/34135-65, (2009).
Sakai et al., "Functional resoration of BRCA2 protein by secondary BRCA2 mutations in BRCA2-mutated ovarian carcinoma", Cancer Res; 2009; 69(16):6381-6386.

(56) References Cited

OTHER PUBLICATIONS

Sakai et al., "Secondary mutations as a mechanism of cisplatin resistance in BRCA2-mutated cancers", Nature; 2008; 451(7182):1116-1120.
Samouelian et al., "Chemosensitivity and radiosensitivity profiles of four new human epithelial ovarian cancer cell lines exhibiting genetic alterations in BRCA2 TGFB-RII KRAS2 TP53 and/or CDNK2A", Cancer Chemother Pharmacol, 2004, 54: 497-504.
Sandhu et al., "The poly(ADP-ribose) polymerase inhibitor niraparib (MK4827) in BRCA mutation carriers and patients with sporadic cancer: a phase 1 dose-escalation trial", Lancet Oncology, 14(9):882-92, Aug. 2013.
Santana-Davila et al., "Treatment Options for Patients With Triple-Negative Breast Cancer", Journal of Hematology & Oncology, 3:42 (Oct. 27, 2010).
Schouten et al., "Challengers in the Use of DNA Repair Deficiency as a Biomarker in Breast Cancer", Journal of Clinical Oncology, 2015, 33(17): 1867-1869.
Schwartz et al., "Homologous recombination and nonhomologous end-joining repair pathways regulate fragile site stability", Genes & Development, 2005, 19: 2715-2726.
Schweiger et al., "Genome-Wide Massively Parallel Sequencing of Formaldehyde Fixed-Paraffin Embedded (FFPE) Tumor Tissues for Copy-Number- and Mutation-Analysis", PLoS ONE, 2009, 4: e5548.
Sebat et al., "Large-Scale Copy Number Polymorphism in the Human Genome", Science, Jul. 2004, 305:525-528.
Shanda et al., "Homologous Recombination Deficiency (HRD) in Patients with Pancreatic Cancer and Response to Chemotherapy", 2017, ASCO presentation.
Silva et al., "Loss of heterozygosity in BRCA1 and BRCA2 markers and high-grade malignancy in breast cancer", Breast Cancer Res. Treat, (Jan. 1999), vol. 53, No. 1, pp. 9-17, XP055076352.
Silver et al., "Efficacy of Neoadjuvant Cisplatin in Triple-Negative Breast Cancer", J. Clin. Oncol. vol. 28, 2010, pp. 1145-1153.
Silver et al., "Further evidence for BRCA1 communication with the inactive X chromosome", Cell, Mar. 2007, 128(5): 991-1002.
Smid et al., "Patterns and incidence of chromosomal instability and their prognostic relevance in breast cancer subtypes", Breast Cancer Research and Treatment, Kluwer Academic Publishers, BO, vol. 128, No. 1, Jul. 15, 2010, pp. 23-30, XP019916000, ISSN: 1573-7217DOI: 10.1007/S10549-010-1026-5.
Sorlie et al., "Repeated observation of breast tumor subtypes in independent gene expression data sets", PNAS, Jul. 2003, 100(14): 8418-8423.
Soule et al., "Isolation and Characterization of a Spontaneously Immortalized Human Breast Epithelial Cell Line, MCF-10", Cancer Research, Sep. 15, 1990, 50: 6075-6086.
Stankiewicz et al., "Genome Architectre Catalyzes Nonrecurrent Chromosomal Rearrangements", Am. J. Hum. Genet., 2003, 72:1101-1116.
Stefansson et al., "Genomic profiling of breast tumours in relation to BRCA abnormalities and phenotypes", Breast Cancer Res; 2009; 11(4):R47, 14 pages.
Stronach et al., "Biomarker Assessment of HR Deficiency, Tumor BRCA1/2 Mutations, and CCNE1 Copy Number in Ovarian Cancer: Associations with Clinical Outcome Following Platinum Monotherapy", Mol Cancer Res. Jul. 2018; 16(7):1103-1111. doi: 10.1158/1541-7786.MCR-18-0034. Epub May 3, 2018.
Swisher et al., "Secondary BRCA1 mutations in BRCA1-mutated ovarian carcinomas with platinum resistance", Cancer Res., Apr. 2008, 68(8): 2581-2586.
Tai et al., "High-Throughput Loss-of-Heterozygosity Study of Chromosome 3p in Lung Cancer Using Single-Nucleotide Polymorphism Markers", Cancer Research, vol. 66, No. 8, Apr. 15, 2006, pp. 4133-4138.
Takahashi et al., "Clonal and Parallel Evolution of Primary Lung Cancers and Their Metastases Revealed by Molecular Dissection of Cancer Cells", Clinical Cancer Research, 13(1): 111-120 (2007).
Tan et al., "'BRCAness' syndrome in ovarian cancer: a case-control study describing the clinical features and outcome of patients with epithelial ovarian cancer associated with BRCA1 and BRCA2 mutations", J Clin Oncol; 2008; 26 (34):5530-5536.
Tassone et al., "BRCAI expression modulates chemosensitivity of BRCAI-defective HCCl937 human breast cancer cells", British Journal of Cancer, 2003, 88: 1285-1291.
Teh et al., "Genomewide Single Nucleotide Polymorphism Microarray Mapping in Basal Cell Carcinomas Unveils Uniparental Disomy as a Key Somatic Event", Cancer Research, vol. 65, No. 19, Oct. 1, 2005 (Oct. 1, 2005), pp. 8597-8603, XP002703167.
Telli et al., "Abstract PD09-04: Homologous Recombination Deficiency (HRD) score predicts pathologic response following neoadjuvant platinum-based therapy in triple-negative and BRCA1/2 mutation-associated breast cancer (BC)", Cancer Research, (Dec. 15, 2012), URL: http://cancerres.aacrjournals.org/content/72/24_Supplement/PD09-04, (Oct. 19, 2016), XP055312264.
Telli et al., "Phase II Study of Gemcitabine, Carboplatin, and Iniparib as Neoadjuvant Therapy for Triple-Negative and BRCA1/2 Mutation-Associated Breast Cancer With Assessment of a Tumor-Based Measure of Genomic Instability: PrECOG0I0", J Clin Oncol, 2015, 1-7.
Timms et al., "Abstract P6-05-10: Association between BRCA 1 /2 status and DNA-based assays for homologous recombination deficiency in breast cancer", Dec. 2013, Abstracts: Thirty-Sixth Annual CTRC-AACR San Antonio, Texas, Breast Cancer Symposium—Dec. 10-14, 2013, 2 pages.
Timms et al., "Association of BRCA 712 defects with genomic scores predictive of DNA damage repair deficiency among breast cancer subtypes," Breast Cancer Research, 2014, 16: 1-9.
Timms et al., "DNA repair deficiences in ovarian cancer: Genomic analysis of high grade serous ovarian tumors from the NOVA Study", 2015, ESMO presentation, 1 page.
Timms et al., "The Molecular Landscape of Genome Instability in Prostate Cancer", 2015, ESMO presentation, 1 page.
Tommasi et al., "655Val and 1170Pro ERBB2 SNPs in familial breast cancer risk and BRCA1 alterations" Cellular Oncology, 2007, 29: 241-248.
Tseng et al., "Genomewide loss of heterozygosity and its clinical associations in non-small cell lung cancer", Int. J. Cancer, Nov. 1, 2005, vol. 117, No. 2, pp. 241-247.
Tuna et al., "Association between Acquired Uniparental Diomy and Homozygous Mutations and HER2/ER/PR Status in Breast Cancer", PLoS One, 2010, vol. 5, No. 11, e15094.
Turner et al., "BRCA1 dysfunction in sporadic basal-like breast cancer," Oncogene, 2007, 26: 2126-2132.
Valeri et al., "High frequency of allelic losses in high-grade prostate cancer is associated with biochemical progression after radical prostatctomy", Urologic Oncology, Elsevier, New York, NY, US, vol. 23, No. 2, Mar. 1, 2005, pp. 87-92, XP027799195, ISSN: 1078-1439 [retrieved on Mar. 1, 2005].
Van Loo et al., "Allele-specific copy number analysis of tumors", PNAS, 2010, 107(39): 16910-16915.
Van Puijenbroek et al., "Mass spectrometry-based loss of heterozygosity analysis of single-nucleotide polymorphism loci in paraffin embedded tumors using the MassEXTEND assay: single-nucleotide polymorphism loss of heterozygosity analysis of the protein tyrosine phosphatase receptor type J in familial colorectal cancer", J Mol Diagn. Nov. 2005;7(5):623-30. doi: 10.1016/S1525-1578(10)60596-X.
Varley et al., "Nested Patch PCR enables highly multiplexed mutation discovery in candidate genes", Genome Research, 2008, 18: 1844-1850.
Volchenboum et al., "Comparison of Primary Neuroblastoma Tumors and Derivative Early-Passage Cell Lines Using Genome-Wide Single Nucleotide Polymorphism Array Analysis", Cancer Research, vol. 69, No. 10, May 12, 2009, pp. 4143-4149.
Vollebergh et al., "Genomic instability in breast and ovarian cancers: Translation into clinical predictive biomarkers", Cell. Mol. Life Sciences CMLS, 69(2):223-245, Sep. 2011.
Vrieling, "Mitotic maneuvers in the light", Nature Genetics, 28:101-102, Jun. 1, 2001.
Walsh et al., "Genome-Wide loss of Heterozygosity and Uniparental Disomy in BRCA1/2-Associated Ovarian Carcinomas", Clin Cancer Res, 14(23):7645 (Dec. 1, 2008).

(56) References Cited

OTHER PUBLICATIONS

Wang et al., "High quality copy number and genotype data from FFPE samples using Molecular Inversion Probe (MIP) microarrays", BMC Med Genomics. Feb. 19, 2009;2:8. doi: 10.1186/1755-8794-2-8.

Wang et al., "Allele quantification using molecular inversion probes (MIP)", Nucleic Acids Res. Nov. 28, 2005;33(21):e183. doi: 10.1093/nar/gni177.

Wang et al., "Analysis of molecular inversion probe performance for allele copy number determination", Genome Biol, 2007, 8(11):R246.

Wang et al., "Loss of heterozygosity and its correlation with expression profiles in subclasses of invasive breast cancers", Cancer Res, Jan. 2004, 64(1): 64-71.

Wilcox et al., "High-resolution methylation analysis of the BRCA1 promoter in ovarian tumors", Cancer Genet Cytogenet; 2005; 159(2): 114-122.

Wilcoxen et al., "Homologous recombination deficiency (HRD) score enriches for niraparib sensitive high grade ovarian tumors", Supplemental Abstract, 2015, 1 page.

Wilcoxen et al., "Use of homologous recombination deficiency (HRD) score to enrich for niraparib sensitive high grade ovarian tumors", J Clin Oncol, 2015, Supplemental Abstract: 5532, 2 pages.

Xiao et al., "The XIST Noncoding RNA Functions Independently of BRCA1 in X Inactivation", Cell, Mar. 2007, 128:977-989.

Xu et al., "Centrosome amplification and a defective G2-M cell cycle checkpoint induce genetic instability in BRCA1 Exon 11 Isoform-deficient cells", Molecular Cell, 1999, 3:389-395.

Yang et al., "Reconstitution of caspase 3 sensitizes MCF-7 breast cancer cells to doxorubicin- and etoposide-induced apoptosis", Cancer Res, Jan. 2001, 61(1): 348-54.

Yaris et al., "Primary cerebral neuroblastoma: a case treated with adjuvant chemotherapy and radiotherapy", The Turkish Journal of Pediatrics, 2004; 46:182-185.

Zhao et al., "Systematic detection of putative tumor suppressor genes through the combined use of exome and transcriptome sequencing", Genome Biol., 2010, vol. 11: R114, pp. 1-14.

Zuchner et al., "Linkage and association study of late-onset Alzheimer disease families linked to 9p21.3", Ann Hum Genet, Nov. 2008, 72(Pt 6): 725.

\* cited by examiner

METHODS AND MATERIALS FOR ASSESSING ALLELIC IMBALANCE

CROSS-REFERENCE TO RELATED APPLICATIONS

This application is a continuation of U.S. application Ser. No. 15/412,404, filed Jan. 23, 2017, which is a continuation of U.S. application Ser. No. 15/010,721, filed Jan. 29, 2016 (issued as U.S. Pat. No. 9,574,229), which is a continuation of U.S. application Ser. No. 14/109,163, filed Dec. 17, 2013 (issued as U.S. Pat. No. 9,279,156), which is a continuation of International Application No. PCT/US12/042668, filed Jun. 15, 2012, which claims the priority benefit of U.S. Provisional Application No. 61/498,418, filed Jun. 17, 2011, the entire contents of each of which are hereby incorporated by reference.

FIELD OF THE INVENTION

The invention generally relates to molecular diagnosis, and particularly to a method and system for detecting allelic imbalance in patient samples.

BACKGROUND OF THE INVENTION

In general, a comparison of sequences present at the same locus on each chromosome (each autosomal chromosome for males) of a chromosome pair can reveal whether that particular locus is homozygous or heterozygous within the genome of a cell. Polymorphic loci within the human genome are generally heterozygous within an individual since that individual typically receives one copy from the biological father and one copy from the biological mother. In some cases, a polymorphic locus or a string of polymorphic loci within an individual are homozygous as a result in inheriting identical copies from both biological parents. In other cases, homozygosity results from a loss of heterozygosity (LOH) from the germline. Because LOH and copy number information can be clinically useful, there is a need for improved methods of identifying loci and regions of LOH in samples.

BRIEF SUMMARY OF THE INVENTION

Copy number (including allelic imbalance and LOH) analysis of tumor tissues has been traditionally performed using single nucleotide polymorphism (SNP) arrays. The data quality is often highly variable and, especially for FFPE samples, tends to be poor. The inventors have developed a method of genome-wide copy number analysis that produces high quality data from all sample types that is based on in-solution capture of DNA fragments spanning target loci (e.g., SNPs), followed by parallel sequencing to identify and quantitate the alleles. The resulting data allows high quality LOH and copy number analysis of the sample.

Accordingly, in one aspect of the present invention, a method of detecting allelic imbalance status in a plurality of genomic loci in a tumor sample from a cancer patient is provided, comprising the steps of enriching a genomic DNA sample for DNA molecules each comprising a locus of interest; sequencing said DNA molecules to determine the genotype at each such locus; determining for each locus whether there is allelic imbalance.

In another aspect of the present invention, a method of detecting LOH status in a plurality of genomic loci in a tumor sample from a cancer patient is provided, comprising the steps of enriching a genomic DNA sample for DNA molecules each comprising a locus of interest; sequencing said DNA molecules to determine the genotype at each such locus; determining for each homozygous locus whether it is homozygous due to LOH.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
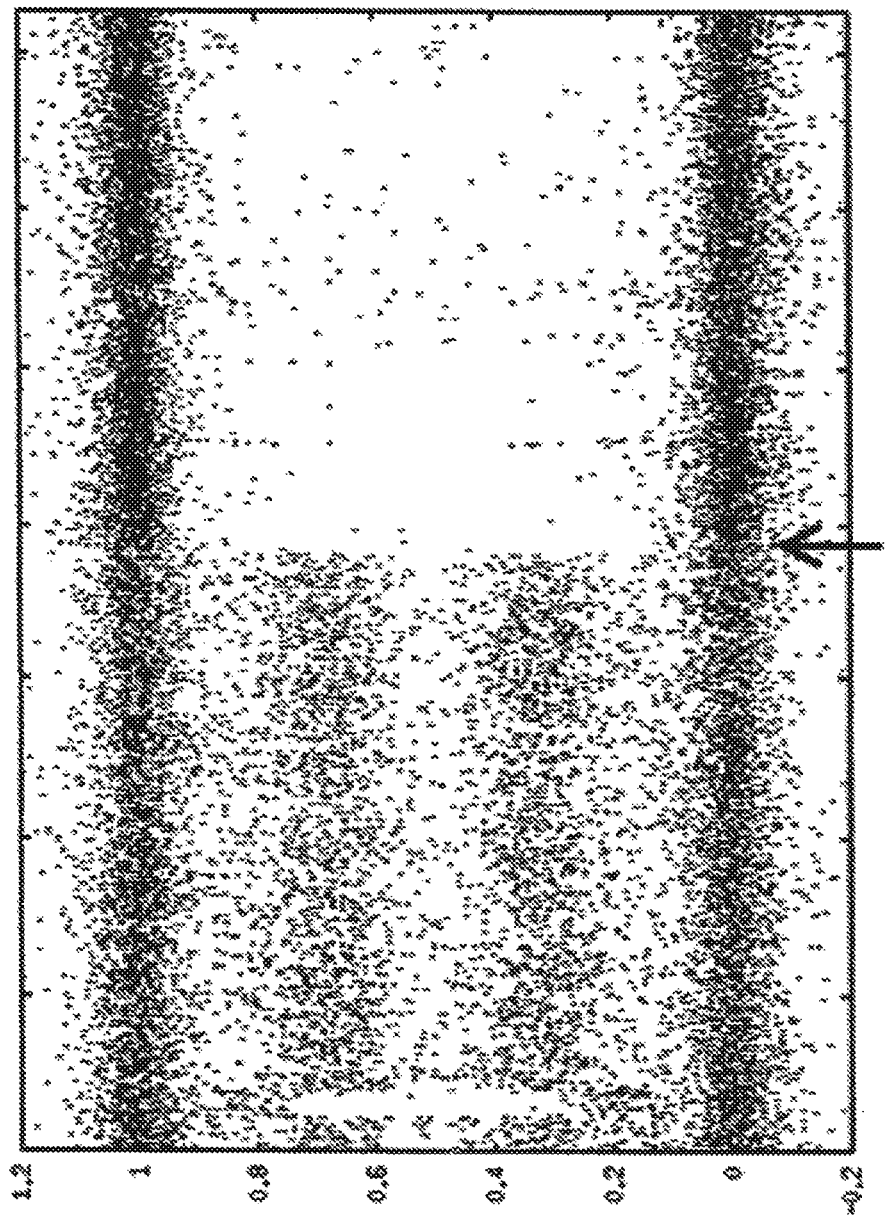
FIG. 1 is a graph plotting allele dosages of breast cancer cells from a breast cancer patient along chromosome 1 as determined using a SNP array. The chromosome region between the arrows is an LOH region that is about 103 Mb in length.

It has been surprisingly discovered that determining allelic imbalance (e.g., abnormal copy number, LOH) in formalin-fixed paraffin-embedded ("FFPE") samples using sequencing of genomic regions comprising loci of interest (e.g., SNPs) yields far superior quality data when compared to copy number and allelic imbalance data generated using microarrays. This invention enables large-scale (e.g., whole genome) copy number (e.g., allelic imbalance) analysis of samples of varying quality. In particular, it enables high quality data to be produced from FFPE-derived DNA. Current array-based platforms are unable to produce data of sufficient quality from this sample type.

Accordingly, in one aspect of the present invention, a method of detecting allelic imbalance status in a plurality of genomic loci in a tumor sample from a cancer patient is provided, comprising the steps of enriching a genomic DNA sample for DNA molecules each comprising a locus of interest; sequencing said DNA molecules to determine the genotype at each such locus; determining for each locus whether there is allelic imbalance. "Locus" as used herein has its usual meaning in the art. As used herein, "region" means a plurality of substantially adjacent loci. Unless stated otherwise or unless the context clearly indicates otherwise, statements made about a locus will generally apply to a region.

As used herein, "allelic imbalance" means any instance where the somatic copy number differs from the germline copy number at a genomic locus or region. In some embodiments allelic imbalance is expressed in terms of major copy proportion ("MCP"). Major copy proportion and MCP, as used herein, mean the ratio of the major allele copy number to the major+minor allele copy number, as follows:

MCP=[major allele copy number]/([major allele copy number]+[minor allele copy number])

In some embodiments, a locus or region shows allelic imbalance if the MCP at such locus or region is 0.51, 0.52, 0.53, 0.54, 0.55, 0.6, 0.65, 0.7, 0.75, 0.8, 0.85, 0.9, 0.95, or 1.

One example of allelic imbalance is loss of heterozygosity ("LOH"), in which a locus is heterozygous in the germline but homozygous in somatic tissue. In this sense, homozygosity can include homozygous loss (i.e., deletion) of the locus in somatic tissue. The different types of possible LOH and allelic imbalance are discussed in more detail below.

Thus in some embodiments the present invention provides a method of detecting LOH status in a plurality of genomic loci in a tumor sample from a cancer patient, comprising enriching a genomic DNA sample for DNA molecules each comprising a locus of interest; sequencing said DNA molecules to determine the genotype at each such locus; determining for each homozygous locus whether it is homozygous due to LOH.

According to the present invention, nucleic acid sequencing techniques can be used to identify loci and/or regions as having allelic imbalance. For example, genomic DNA from a cell sample (e.g., a cancer cell sample) can be extracted and fragmented. Any appropriate method can be used to extract and fragment genomic nucleic acid including, without limitation, commercial kits such as QIAamp DNA Mini Kit (Qiagen), MagNA Pure DNA Isolation Kit (Roche Applied Science) and GenElute Mammalian Genomic DNA Miniprep Kit (Sigma-Aldrich). Once extracted and fragmented, either targeted or untargeted sequencing can be done to determine the sample's genotypes at loci of interest. For example, whole genome, whole transcriptome, or whole exome sequencing can be done to determine genotypes at millions or even billions of base pairs (i.e., base pairs can be "loci" to be evaluated).

In some cases, targeted sequencing of known polymorphic loci (e.g., SNPs and surrounding sequences) can be done as an alternative to microarray analysis. For example, the genomic DNA can be enriched for those fragments containing a locus (e.g., SNP location) to be analyzed using kits designed for this purpose (e.g., Agilent SureSelect, Illumina TruSeq Capture, Nimblegen SeqCap EZ Choice, Raindance Thunderstorm™). For example, genomic DNA containing the loci to be analyzed can be hybridized to biotinylated capture RNA fragments to form biotinylated RNA/genomic DNA complexes. Alternatively, DNA capture probes may be utilized resulting in the formation of biotinylated DNA/genomic DNA hybrids. Streptavidin coated magnetic beads and a magnetic force can be used to separate the biotinylated RNA/genomic DNA complexes from those genomic DNA fragments not present within a biotinylated RNA/genomic DNA complex. The obtained biotinylated RNA/genomic DNA complexes can be treated to remove the captured RNA from the magnetic beads, thereby leaving intact genomic DNA fragments containing a locus to be analyzed. These intact genomic DNA fragments containing the loci to be analyzed can be amplified using, for example, PCR techniques. Alternatively, a multiplex PCR reaction can be employed to enrich for loci of interest. PCR primers can be designed to flank loci of interest and a PCR reaction can be run to amplify sequences comprising such loci.

The enriched genomic DNA fragments can be sequenced using any sequencing technique. Beyond Sanger sequencing, numerous suitable sequencing machines and strategies are well known in the art, including but not limited to those developed by Illumina (the Genome Analyzer; Bennett et al. (2005) Pharmacogenomics, 6:373-382; HiSeq; MiSeq); by Applied Biosystems, Inc. (the SOLiD™ Sequencer; solid.appliedbiosystems.com); by Roche (e.g., the 454 GS FLX™ sequencer; Margulies et al. (2005) Nature, 437:376-380; U.S. Pat. Nos. 6,274,320; 6,258,568; 6,210,891); by Helicos Biosciences (Heliscope™ system, see, e.g., U.S. Patent App. Pub. No. 2007/0070349); by Oxford Nanopore (e.g., GridION™ and MinION™, see, e.g., International Application No. PCT/GB2009/001690, pub. no. WO/2010/004273); and by others.

The sequencing results from the genomic DNA fragments can be used to identify loci as having allelic imbalance. In some cases, an analysis of the allelic imbalance status of loci over a length of a chromosome can be performed to determine the length of regions of allelic imbalance. For example, a stretch of SNP locations that are spaced apart (e.g., spaced about 25 kb to about 100 kb apart) along a chromosome can be evaluated by sequencing, and the sequencing results used to determine not only the presence of a region of allelic imbalance ( ) e.g., somatic homozygosity) along a chromosome but also the length of that region of imbalance. Obtained sequencing results can be used to generate a graph that plots allele dosages along a chromosome. Allele dosage $d_i$ for SNP i can be calculated from the adjusted number of captured probes for two alleles ($A_i$ and $B_i$): $d_i=A_i/(A_i+B_i)$. An example of such a graph is presented in FIG. 2.

Once a sample's genotype (e.g., homozygosity) has been determined for a plurality of loci (e.g., SNPs), common techniques can be used to identify loci and regions of allelic imbalance due to somatic change (e.g., LOH). One way to determine whether imbalance is due to somatic change is to compare the somatic genotype to the germline. For example, the genotype for a plurality of loci (e.g., SNPs) can be determined in both a germline (e.g., blood) sample and a somatic (e.g., tumor) sample. The genotypes for each sample can be compared (typically computationally) to determine where the genome of the germline cell was, e.g., heterozygous and the genome of the somatic cell is, e.g., homozygous. Such loci are LOH loci and regions of such loci are LOH regions.

Computational techniques can also be used to determine whether allelic imbalance is somatic (e.g., due to LOH). Such techniques are particularly useful when a germline sample is not available for analysis and comparison. For example, algorithms such as those described elsewhere can be used to detect allelic imbalance regions using information from SNP arrays (Nannya et al., *Cancer Res.*, 65:6071-6079 (2005)). Typically these algorithms do not explicitly take into account contamination of tumor samples with benign tissue. Cf. International Application No. PCT/US2011/026098 to Abkevich et al.; Goransson et al., PLoS One (2009) 4(6):e6057. This contamination is often high enough to make the detection of allelic imbalance regions challenging. Improved analytical methods according to the present invention for identifying allelic imbalance, even in spite of contamination, include those embodied in computer software products as described below.

The following is one example. If the observed ratio (e.g., MCP) of the signals of two alleles, A and B, is two to one, there are two possibilities. The first possibility is that cancer cells have LOH with deletion of allele B in a sample with 50% contamination with normal cells. The second possibility is that there is no LOH but allele A is duplicated in a sample with no contamination with normal cells. An algorithm can be implemented as a computer program as described herein to reconstruct LOH regions based on genotype (e.g., SNP genotype) data. One point of the algorithm is to first reconstruct allele specific copy numbers (ASCN) at each locus (e.g., SNP). ASCNs are the numbers of copies of both paternal and maternal alleles. An LOH region is then determined as a stretch of SNPs with one of the ASCNs (paternal or maternal) being zero. The algorithm can be based on maximizing a likelihood function and can be conceptually akin to a previously described algorithm designed to reconstruct total copy number (rather than ASCN) at each locus (e.g., SNP). See International Application No. PCT/US2011/026098 (pub. no. WO/2011/106541) (hereby incorporated by reference in its entirety). The likelihood function can be maximized over ASCN of all loci, level of contamination with benign tissue, total copy number averaged over the whole genome, and sample specific noise level. The input data for the algorithm can include or consist of (1) sample-specific normalized signal intensities for both allele of each locus and (2) assay-specific (specific for different SNP arrays and for sequence based approach) set of parameters defined based on analysis of large number of samples with known ASCN profiles.

In some cases, a selection process can be used to select loci (e.g., SNP loci) to be evaluated using an assay configured to identify loci as having allelic imbalance (e.g., SNP array-based assays and sequencing-based assays). For example, any human SNP location can be selected for inclusion in a SNP array-based assay or a sequencing-based assay configured to identify loci as having allelic imbalance within the genome of cells. In some cases, 0.5, 1.0, 1.5, 2.0, 2.5 million or more loci (e.g., SNP locations) present within the human genome can be evaluated to identify those loci that (a) are not present on the Y chromosome, (b) are not mitochondrial loci, (c) have a minor allele frequency of at least about 5% in the population of interest (e.g., Caucasians), (d) have a minor allele frequency of at least about 1% in three populations other than the population of interest (e.g., Chinese, Japanese, and Yoruba), and/or (e) do not have a significant deviation from Hardy-Weinberg equilibrium in any of these populations. In some cases, more than 100,000, 150,000, or 200,000 human loci can be selected that meet criteria (a) through (e). Of the human loci meeting criteria (a) through (e), a group of loci (e.g., top 2,500, 5,000, 7,500, 10,000, 20,000, 30,000, 40,000, 50,000, 75,000, 100,000, 150,000, or 200,000 loci) can be selected such that the loci have a high degree of allele frequency in the population of interest, cover the human genome in a somewhat evenly spaced manner (e.g., at least one locus of interest every about 5 kb, 10 kb, 25 kb, 50 kb, 75 kb, 100 kb, 150 kb, 200 kb, 300 kb, 400 kb, 500 kb or more), and are not in linkage disequilibrium with another selected locus in any of the populations used for analysis. In some cases, about 40, 50, 60, 70, 80, 90, 100, 110, 120, 130 thousand or more loci can be selected as meeting each of these criteria and included in an assay configured to identify allelic imbalance regions across a human genome. For example, between about 70,000 and about 90,000 (e.g., about 80,000) SNPs can be selected for analysis with a SNP array-based assay, and between about 45,000 and about 55,000 (e.g., about 54,000) SNPs can be selected for analysis with a sequencing-based assay.

Accordingly, in one aspect of the present invention, a method of detecting allelic imbalance status in a plurality of genomic loci in a sample from a patient is provided, comprising the steps of enriching a genomic DNA sample for DNA molecules each comprising a locus of interest; sequencing said DNA molecules to determine the genotype at each such locus; determining for each locus whether it has allelic imbalance.

In another aspect of the present invention, a method of detecting LOH status in a plurality of genomic loci in a sample from a patient is provided, comprising the steps of enriching a genomic DNA sample for DNA molecules each comprising a locus of interest; sequencing said DNA molecules to determine the genotype at each such locus; determining for each homozygous locus whether it is homozygous due to LOH.

In another aspect of the present invention, a method of detecting copy number status in a plurality of genomic loci in a sample from a patient is provided, comprising the steps of enriching a genomic DNA sample for DNA molecules each comprising a locus of interest; sequencing said DNA molecules; and quantitating each allele at each such locus to determine its copy number.

In some embodiments at least 10, 50, 100, 1,000, 10,000, 50,000, 55,000, 75,000, 100,000, 150,000, 200,000, 300,000, 400,000, 500,000, 750,000, 1,000,000, 2,000,000 or more loci are evaluated. In some embodiments these loci are spaced evenly along the genome. As used herein, loci are "evenly spaced along the genome" when the percentage difference between the $distance_{AB}$ between any two loci A and B and the $distance_{CD}$ between any other two loci C and D (i.e., $100*(distance_{AB}-distance_{CD})/distance_{AB}$ or $100*(distance_{AB}-distance_{CD})/distance_{CD}$) is less than or equal to 50%, 40%, 30%, 20%, 15%, 10%, 9%, 8%, 7%, 6%, 5%, 4%, 3%, 2%, or 1%. Such percentage difference is referred to herein as the "genomic spacing" of loci. In some embodiments the sample is an FFPE tissue sample. In some embodiments the sample is a tumor sample from the patient.

Another aspect of the invention provides a system for determining allelic imbalance status in a plurality of loci in a sample comprising: a sample analyzer for (1) enriching a genomic DNA sample for DNA molecules each comprising a locus of interest and (2) sequencing said DNA molecules to produce a plurality of quantitative signals about each such locus; a computer program for analyzing said plurality of quantitative signals to determine whether each such locus has allelic imbalance.

Another aspect of the invention provides a system for determining LOH status in a plurality of loci in a sample comprising: a sample analyzer for (1) enriching a genomic DNA sample for DNA molecules each comprising a locus of interest and (2) sequencing said DNA molecules to produce a plurality of quantitative signals about each such locus; a computer program for analyzing said plurality of quantitative signals to determine whether each such locus is homozygous in the sample; and a computer program for determining for each homozygous locus whether it is homozygous due to LOH.

Another aspect of the invention provides a system for detecting copy number status in a plurality of genomic loci in a sample from a patient comprising: a sample analyzer for (1) enriching a genomic DNA sample for DNA molecules each comprising a locus of interest and (2) sequencing said DNA molecules to produce a plurality of quantitative signals about each such locus; and a computer program for analyzing said plurality of quantitative signals to quantitate each allele at each such locus to determine its copy number.

In some embodiments of the systems of the invention, one sample analyzer both enriches the sample for DNA of interest and sequences that DNA. In other embodiments two or more sample analyzers perform these functions. In some embodiments, one software program analyzes the plurality of quantitative signals to determine whether each locus is homozygous in the sample and also determines for each homozygous locus whether it is homozygous due to LOH.

Figure 3:
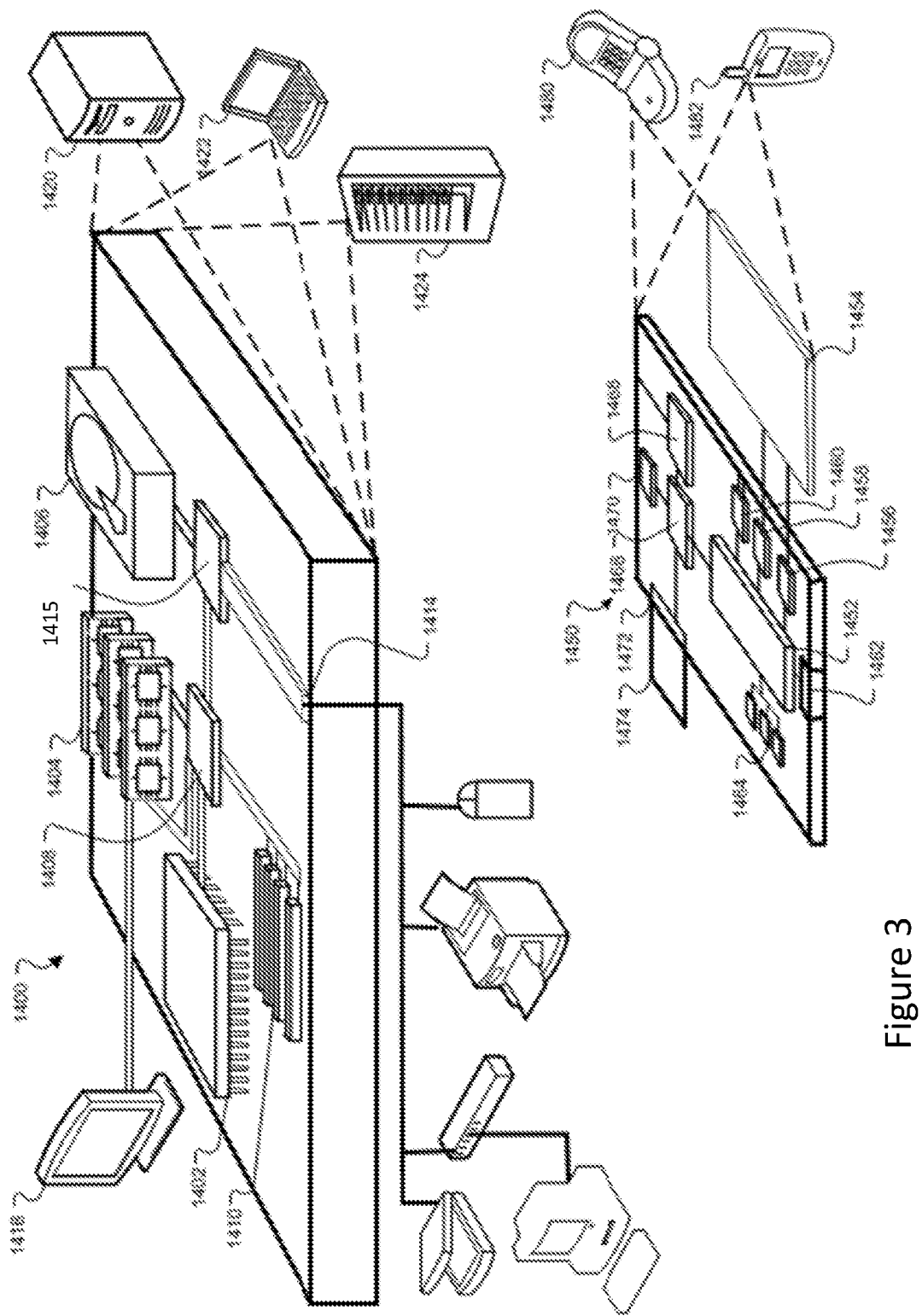
FIG. 3 is a diagram of an example of a computer device and a mobile computer device that can be used to implement the techniques described herein.

FIG. 3 is a diagram of an example of a computer device 1400 and a mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some cases, a system provided herein can be configured to include one or more sample analyzers. A sample analyzer can be configured to produce a plurality of signals about genomic DNA of a cancer cell. For example, a sample analyzer can produce signals that are capable of being interpreted in a manner that identifies the allelic imbalance status of loci along a chromosome. In some cases, a sample analyzer can be configured to carry out one or more steps of a sequencing-based assay and can be configured to produce and/or capture signals from such assays. In some cases, a computing system provided herein can be configured to include a computing device. In such cases, the computing device can be configured to receive signals from a sample analyzer.

The computing device can include computer-executable instructions or a computer program (e.g., software) containing computer-executable instructions for carrying out one or more of the methods or steps described herein. In some cases, such computer-executable instructions can instruct a computing device to analyze signals from a sample analyzer, from another computing device, or from a sequencing-based assay. The analysis of such signals can be carried out to determine genotypes, allelic imbalance at certain loci, regions of allelic imbalance, the number of allelic imbalance regions, to determine the size of allelic imbalance regions, to determine the number of allelic imbalance regions having a particular size or range of sizes, or to determine a combination of these items.

In some cases, a system provided herein can include computer-executable instructions or a computer program (e.g., software) containing computer-executable instructions for formatting an output providing an indication about copy number, allelic imbalance, LOH, or a combination of these items.

In some cases, a system provided herein can include a pre-processing device configured to process a sample (e.g., cancer cells) such that a sequencing-based assay can be performed. Examples of pre-processing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

Additional embodiments of the invention are as follows:

Embodiment 1

An in vitro method of detecting allelic imbalance status in a plurality of genomic loci in a sample from a patient, comprising:
  enriching a genomic DNA sample for DNA molecules each comprising a locus of interest;
  sequencing said DNA molecules to determine the genotype at each such locus;
  determining for each locus whether it has allelic imbalance.

Embodiment 2

An in vitro method of detecting LOH status in a plurality of genomic loci in a sample from a patient, comprising:
  enriching a genomic DNA sample for DNA molecules each comprising a locus of interest;
  sequencing said DNA molecules to determine the genotype at each such locus;
  determining for each homozygous locus whether it is homozygous due to LOH.

Embodiment 3

A system for determining allelic imbalance status in a plurality of genomic loci in a sample comprising:
  a sample analyzer for (1) enriching a genomic DNA sample for DNA molecules each comprising a locus of interest and (2) sequencing said DNA molecules to produce a plurality of quantitative signals about each such locus;
  a computer program for analyzing said plurality of quantitative signals to determine the genotype of each such locus in the sample; and
  a computer program for determining for each locus whether it has allelic imbalance.

Embodiment 4

A system for determining LOH status in a plurality of genomic loci in a sample comprising:
  a sample analyzer for (1) enriching a genomic DNA sample for DNA molecules each comprising a locus of interest and (2) sequencing said DNA molecules to produce a plurality of quantitative signals about each such locus;
  a computer program means for analyzing said plurality of quantitative signals to determine the genotype of each such locus in the sample; and
  a computer means for determining for each homozygous locus whether it is homozygous due to LOH.

Embodiment 5

The method of either Embodiment 1 or Embodiment 2 or the system of either Embodiment 3 or Embodiment 4, wherein said plurality of genomic loci comprises at least 10, 50, 100, 1,000, 10,000, 50,000, 55,000, 75,000, 100,000, 150,000, 200,000, 300,000, 400,000, 500,000, 750,000, 1,000,000, or 2,000,000 or more loci.

Embodiment 6

The method or system of Embodiment 5, wherein said genomic loci are evenly spaced along the genome.

Embodiment 7

The method or system of Embodiment 6, wherein the genomic spacing of said plurality of genomic loci is less than or equal to 50%, 40%, 30%, 20%, 15%, 10%, 9%, 8%, 7%, 6%, 5%, 4%, 3%, 2%, or 1%.

Embodiment 8

The method of either Embodiment 1 or Embodiment 2 or the system of either Embodiment 3 or Embodiment 4, wherein said sample is a formalin-fixed, paraffin-embedded tissue sample.

Embodiment 9

The method or system of Embodiment 8, wherein said sample is a tumor sample extracted from the patient.

Examples

The process described here utilized an Agilent SureSelect Capture system followed by Illumina HiSeq sequencing, however any in solution or solid support based capture method and high throughput parallel sequencing platform could be used.

The initial design selection process utilized the ~2.5 million SNPs on the Illumina Omni2.5 SNP array. This list of SNPs was chosen because it is the currently the largest list of SNPs from which there is genotyping information available for multiple different population groups. All 2,448,785 SNP locations were input into the Agilent eArray Sure Select Target Enrichment wizard for Single End Long Reads using the default settings. 1,353,042 passed the selection criteria and had baits designed.

Then, 110,000 SNPs with high minor allele frequencies and evenly covering the genome were selected. In the selection, SNPs in strong linkage disequilibriom and SNPs with stong deviation from Hardy-Weinberg equilibrium were discarded.

Two preliminary library designs were constructed comprised of 55,000 probes each targeting 55,000 different SNP locations. Testing was carried out using a high quality normal DNA sample to check for even capture of both alleles of every SNP. In addition, 4 FFPE samples were captured and used to select the most optimally performing probes. We looked for probes that showed robust capture and even sequence depth without over or underrepresentation of sequence reads in the final sequencing library.

The final capture probe library design was comprised of the 55,000 optimal probes identified using the preliminary capture designs.

Figure 2:
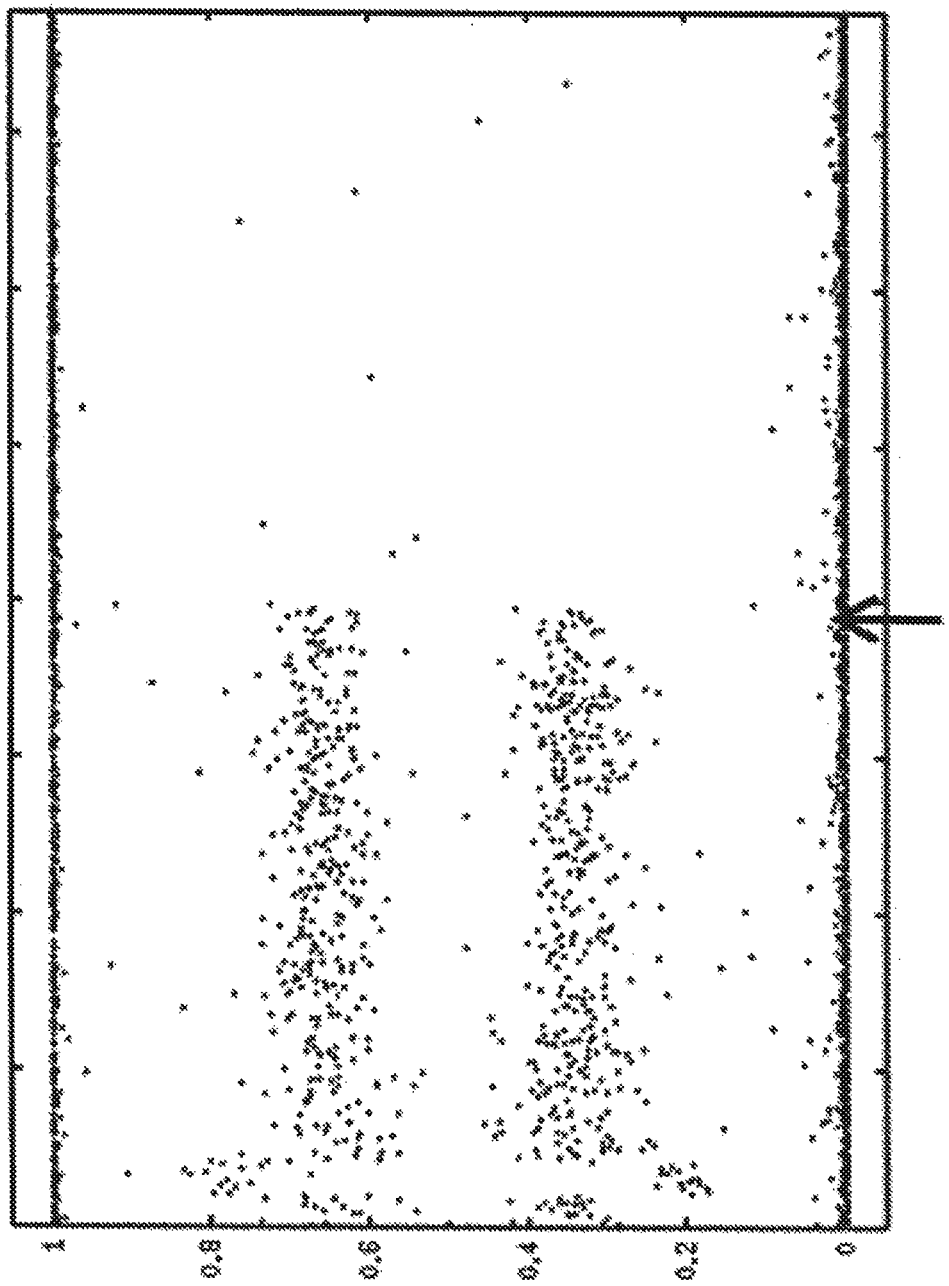
FIG. 2 is a graph plotting allele dosages of breast cancer cells for the same breast cancer patient as on FIG. 1 along chromosome 1 as determined using high-throughput sequencing. The chromosome region between the arrows is an LOH region that is about 103 Mb in length.

The results of measuring copy number and LOH using the above sequencing technique are shown in FIG. 2 (with FIG. 1 showing microarray analysis on fresh frozen tissue as a comparison).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. An in vitro method of detecting loss of heterozygosity (LOH) status in a plurality of single nucleotide polymorphism (SNP) genomic loci in a formalin-fixed paraffin-embedded tissue sample from a patient, comprising:
    enriching a genomic DNA sample for DNA molecules each comprising a SNP locus of interest, wherein there is at least one SNP locus located on average every 5 Mb within each chromosome that is examined;
    sequencing the DNA molecules to determine the genotype at each such SNP locus;
    determining for each homozygous SNP locus whether it is homozygous due to LOH.

2. The method of claim 1, wherein there is at least one SNP locus located on average every 1 Mb within each chromosome that is examined.

3. The method of claim 1, wherein the plurality of genomic SNP loci comprises at least 5,000 more loci.

4. The method of claim 1, wherein the plurality of genomic SNP loci comprises at least 10,000 more loci.

5. The method of claim 1, wherein a SNP locus is determined to have allelic imbalance if the major copy proportion at the SNP locus is 0.51 or greater.

6. The method of claim 1, wherein the SNP genomic loci are evenly spaced along the genome.

7. The method of claim 6, wherein the percentage difference between the distance between any two of the plurality of SNP genomic loci and the distance between any other two of the plurality of SNP loci is less than or equal to 20%.

8. The method of claim 1, wherein the sample is a tumor sample extracted from the patient.

9. The method of claim 8, wherein the tumor sample comprises at least 5%, or more contamination with non-tumor cells.

10. The method of claim 1, wherein there is at least one single nucleotide polymorphism locus located on average every 500 kb within each chromosome.

11. A system for determining LOH status in a plurality of SNP genomic loci in a formalin-fixed paraffin-embedded tissue sample, wherein the system comprises:
    a sample analyzer configured to
        enrich a genomic DNA sample for DNA molecules, each test DNA molecule comprising a SNP locus of interest and wherein there is at least one SNP locus located on average every 5 Mb within each chromosome that is examined;
        sequencing the DNA molecules to produce a plurality of quantitative signals for each such SNP locus;
    a computer program that is configured to analyze the plurality of quantitative signals to determine the genotype of each such SNP locus in the sample; and
    a computer program that is configured to determine, for each homozygous SNP locus, whether the locus is homozygous due to LOH.

12. The system of claim 11, wherein there is at least one SNP locus located on average every 1 Mb within each chromosome that is examined.

13. The system of claim 11, wherein the plurality of genomic SNP loci comprises at least 5,000 more loci.

14. The system of claim 11, wherein the plurality of genomic SNP loci comprises at least 10,000 more loci.

15. The system of claim 11, wherein a SNP locus is determined to have allelic imbalance if the major copy proportion at the SNP locus is 0.51 or greater.

16. The system of claim 11, wherein the SNP genomic loci are evenly spaced along the genome.

17. The system of claim 16, wherein the percentage difference between the distance between any two of the plurality of SNP genomic loci and the distance between any other two of the plurality of SNP loci is less than or equal to 20%.

18. The system of claim 11, wherein the sample is a tumor sample extracted from the patient.

19. The system of claim 18, wherein the tumor sample comprises at least 5%, or more contamination with non-tumor cells.

20. The system of claim 11, wherein there is at least one single nucleotide polymorphism locus located on average every 500 kb within each chromosome.

* * * * *